US006693397B2

(12) United States Patent
Handa et al.

(10) Patent No.: US 6,693,397 B2
(45) Date of Patent: Feb. 17, 2004

(54) LIGHT SOURCE DEVICE

(75) Inventors: Keiji Handa, Hachioji (JP); Masanori Yajima, Hachioji (JP); Keisuke Miura, Hachioji (JP); Nobuyuki Furukawa, Hachioji (JP); Shinya Masuda, Hachioji (JP); Keiji Shioda, Hachioji (JP); Takeaki Nakamura, Hino (JP)

(73) Assignee: Olympus Corporation, Tokyo (JP)

( * ) Notice: Subject to any disclaimer, the term of this patent is extended or adjusted under 35 U.S.C. 154(b) by 0 days.

(21) Appl. No.: 10/209,200

(22) Filed: Jul. 31, 2002

(65) Prior Publication Data

US 2003/0060682 A1 Mar. 27, 2003

(30) Foreign Application Priority Data

Aug. 23, 2001 (JP) .......................... 2001-253369

(51) Int. Cl.[7] .............................. G05F 1/00; H05B 37/02
(52) U.S. Cl. ....................... 315/291; 315/307; 315/360
(58) Field of Search ................. 315/291, 302, 315/307, 308, 318, 360, 362; 343/872, 892; 600/28; G05F 1/00; H05B 37/02

(56) References Cited

U.S. PATENT DOCUMENTS 6,495,973 B1 * 12/2002 Allen, Jr. .................. 315/302
6,501,237 B2 * 12/2002 Davies ...................... 315/362
2001/0027997 A1 * 10/2001 Cocuzza et al. ............. 235/454
2002/0005697 A1 * 1/2002 Morgan et al. ............. 315/291
2003/0080901 A1 * 5/2003 Piotrowski ................. 342/386

FOREIGN PATENT DOCUMENTS

| JP | 10-268071 | 10/1998 | ............ A61B/1/06 |
| JP | 2000-126124 | 5/2000 | ............ A61B/1/06 |

* cited by examiner

*Primary Examiner*—Don Wong
*Assistant Examiner*—Trinh Vo Dinh
(74) *Attorney, Agent, or Firm*—Scully, Scott, Murphy & Presser

(57) ABSTRACT

A light-source device includes a lamp unit having a light-source lamp and a device housing which is provided with a lamp-unit container for containing the lamp unit in a removable manner. The device housing includes a CPU for measuring the illumination time of the light-source lamp and an antenna for sending the illumination time measured by the CPU to the lamp unit. The lamp unit includes an RFID tag which is fixed thereto. The RFID tag is provided with an antenna for receiving the illumination time information sent from the antenna of the housing and a rewritable memory for storing the illumination time information received by the antenna of the tag.

20 Claims, 6 Drawing Sheets

| LAMP UNIT STANDARD VALUES AT DELIVERY TIME | CURRENT VALUE |
|---|---|
| 3.0-3.5 | 18.5A |
| 3.5-4.0 | 18.0A |
| 4.0-4.5 | 17.5A |

LIGHT SOURCE DEVICE

This application claims benefit of Japanese Application No. 2001-253369 filed in Japan on Aug. 23, 2001, the contents of which are incorporated by this reference.

BACKGROUND OF THE INVENTION

1. Field of the Invention

The present invention relates to a light-source device, and more particularly, to a light-source device which emits illuminating light to be used in an endoscope, for example.

2. Description of the Related Art

In light-source devices used in, for example, endoscopes, the light-source lamp electrically wears out as a result of feeding electricity. Thus, in order to inform the user when the light-source lamp needs to be replaced, the conventional light-source devices are equipped with a lifetime meter for measuring and displaying the accumulated illumination time of the lamp.

An endoscope light-source device having the lifetime meter described above has been proposed, for example, in Japanese Unexamined Patent Application Publication Nos. 10-268071 and 2000-126124, which were previously filed by the present applicant.

An endoscope light-source device having the conventional lifetime meter like this has the configuration, for example, shown in FIGS. 8 and 9.

FIG. 8 is a perspective view and a partly enlarged view illustrating an endoscope light-source device having a conventional lifetime meter, and FIG. 9 is a block diagram illustrating the configuration of an endoscope light-source device shown in FIG. 8.

As shown in FIG. 8, a light-source device 30 has a lamp-unit replacement door 32 on one side of a device housing 31 in an openable/closable manner. The light-source device 30 has a lamp-unit container 33 which is accessed through an opening covered by the lamp-unit replacement door 32 in the device housing 31.

In the lamp-unit container 33, a lamp-unit mounting/demounting detection switch 34, which is a leaf switch, is disposed on the bottom face. At the same time, the lamp unit 37 consists of a light-source lamp 35 for emitting illuminating light and heat sinks 36.

The light-source lamp 35 uses, for example, a xenon lamp. Thus, the lamp unit 37 is formed by covering the light-source lamp 35 with the heat sinks 36 in order to cool the anode and the cathode of the light-source lamp 35.

In the light-source device 30 having such a configuration, when the lamp unit 37 is installed in the lamp-unit container 33, the lamp-unit mounting/demounting detection switch 34 detects this action. Then, in the light-source device 30, a lamp-replacement detection circuit 38 (refer to FIG. 9) operates to supply the necessary current for illuminating the lamp from a power-supply circuit 39 to the light-source lamp 35.

In the light-source device 30 described above, as shown in FIG. 9, within the device housing 31, the lamp-unit container 33, the power-supply circuit 39, a control circuit 44, a condenser lens 41, a diaphragm 42, and a light-guide connector 43 are appropriately disposed.

The above-described control circuit 44 has the above-described lamp-replacement detection circuit 38, a CPU (Central Processing Unit) 45, and an EEPROM (Electrically Erasable Programmable Read-only Memory) 46. When the light-source lamp 35 is lit, the power-supply circuit 39 sends an illumination signal to the control circuit 44.

Next, the CPU 45 measures the operating time in order to record it as the illumination time based on the illumination signal, and monitors the illumination time. The CPU 45 accumulates and writes the illumination time into the EEPROM 46, in which information data is electrically rewritable.

This means that when the power of the light-source device 30 is turned on, the CPU 45 reads the total operating time data stored in the EEPROM 46, and measures the illumination time of the light-source lamp 35 to be added to the total operating time.

Also, the light-source device 30 has a lifetime meter 50 on a front panel 49 of the device housing 31. The lifetime meter 50 displays the total operating time (accumulated operating time) that the light-source lamp 35 has been lit. In this way, in the light-source device 30, the above-described lifetime meter 50 gives an indication of whether or not the light-source lamp 35 has reached the end of its lifetime.

The front panel 49 is connected to the CPU 45 of the control circuit 44. As shown in the enlarged view of FIG. 8, the front panel 49 includes a display part 50a of the lifetime meter 50, an automatic light control/manual light control changing-over switch 51, a brightness setting-up switch 52a, a brightness setting-down switch 52b, and so on.

Also, as shown in FIG. 9, in the light-source device 30, the condenser lens 41 is disposed on the optical axis O of the light-source lamp 35 and opposes the light-source lamp 35.

The illuminating light of the light-source lamp 35 is condensed by the condenser lens 41, and strikes the end face of the light-guide connector 43 through the diaphragm 42. The light-guide connector 43 is connected to a light-guide cap 47 which is attached to the front face of the device housing 31. The light-guide connector 43 supplies the illuminating light of the light-source lamp 35 to a light-guide cable 48 which is attached to the light-guide cap 47. The light-guide cable 48 transmits the illuminating light to a light guide of the endoscope, which is not shown in the figure. Then the endoscope irradiates the illuminating light transmitted by the light guide to an object.

In this regard, external power is supplied to the above-described power-supply circuit 39 by connecting the plug of a power cable 53 to a power outlet and turning on the power switch.

In the conventional endoscope having such a configuration, the above-described light-source lamp 35 is an electrically consumable item. Consequently, when the above-described light-source lamp 35 is illuminated for a long time, the amount of light emitted decreases.

In this case, when the endoscope irradiates light on the object such as a diseased part of a body through the light guide, the amount of the light decreases. Thus the endoscopic image obtained by the endoscope through its observation optical system becomes dim.

In order to eliminate such a defect, in the conventional endoscope light-source device, the lifetime of the light-source lamp 35 is reported by the lifetime meter 50 so that the light-source lamp 35 can be replaced with a new one.

However, in the case of the endoscope light-source device having the conventional lifetime meter, for example, when interchangeably using various lamp units having different illumination currents and so on, the CPU 45 cannot identify each of the lamp units.

Consequently, in the case of the above-described conventional endoscope light-source device, when totaling the illumination time in EEPROM 46 on the assumption that the same lamp unit is used, the reliability of the time displayed by the lifetime meter 50 might be too low.

Also, in the case of the conventional endoscope light-source device, an increase in the number of illuminations of the light-source lamp might shorten its lifetime, thus it has not been possible to get accurate information for individual light-source lamps.

Furthermore, in the case of the conventional endoscope light-source device, the user might mistakenly reset the lifetime meter without changing the light-source lamp. Consequently, in the case of the conventional endoscope light-source device, the total operating time displayed on the lifetime meter does not necessarily indicate the actual operating time of the light-source lamp.

SUMMARY OF THE INVENTION

Accordingly, it is an object of the present invention to provide a light-source device to be used for an endoscope and so on which can provide accurate information on light-source lamps by storing the information, such as the operating time of the light-source lamp and the number of illuminations, in each of the light-source lamps.

Also, it is another object of the present invention to provide a light-source device which can prevent fluctuation of the light level of the light-source lamp and which can easily provide the optimum light level.

According to a first aspect of the present invention, there is provided a light-source device including: a lamp unit having a light-source lamp; a container part for containing the lamp unit in a removable manner; a counter for measuring illumination time of the light-source lamp when the lamp unit is installed in the container part; a first antenna for sending the illumination time information measured by the counter to the lamp unit; a second antenna, which is provided in the lamp unit, for receiving the illumination time information which is sent from the first antenna; and a rewritable memory, which is provided in the lamp unit, for storing the illumination time information received by the second antenna.

Also, according to a second aspect of the present invention, there is provided a light-source device including: a lamp unit having a light-source lamp; a device housing having a container part for containing the lamp unit in a removable manner; a counter, which is provided in the device housing, for measuring illumination time of the light-source lamp; a first antenna, which is provided in the device housing, for sending illumination time information measured by the counter to the lamp unit; a controller, which is provided in the device housing, for demodulating the illumination time information received by the first antenna to output the information to the counter and for modulating illumination time information measured by the counter to output the information to the first antenna; a second antenna, which is provided in the lamp unit, for receiving the illumination time information which is sent from the first antenna; a rewritable memory, which is provided in the lamp unit, for storing the illumination time information received by the second antenna; and a modulator-demodulator circuit, which is provided in the lamp unit, for reading and modulating illumination time information stored in the memory to output the information to the second antenna and for demodulating the illumination time information received by the second antenna to write the information into the memory.

Furthermore, according to a third aspect of the present invention, there is provided a light-source device including:
a lamp unit having a light-source lamp; a device housing having a container part for containing the lamp unit in a removable manner; a rewritable memory for storing illumination time information of the light-source lamp; reading means for reading the illumination time information from the memory; a counter for measuring illumination time of the light-source lamp and adding the measured illumination time to the total illumination time which has been read by the reading means; and writing means for writing the total illumination time information to which the illumination time has been added by the counter into the memory.

The other features and benefits of the present invention will become fully apparent with the following description.

DESCRIPTION OF THE PREFERRED EMBODIMENTS

In the following, a description will be given of the embodiments of the present invention with reference to the drawings.

(First Embodiment)

Figure 1:
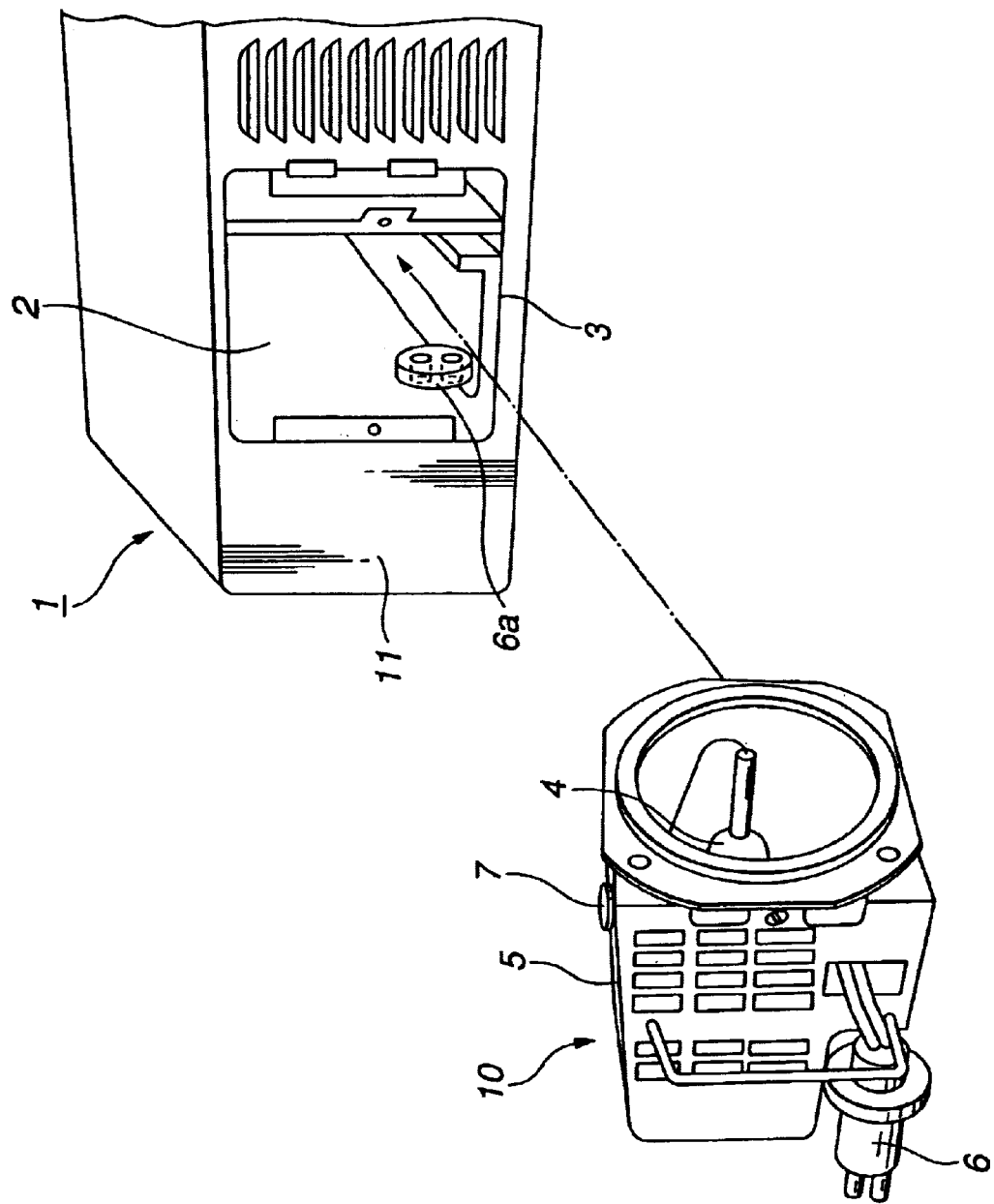
FIG. 1 is a perspective view of a light-source device housing and a lamp unit illustrating a first embodiment of the present invention.
Figure 2:
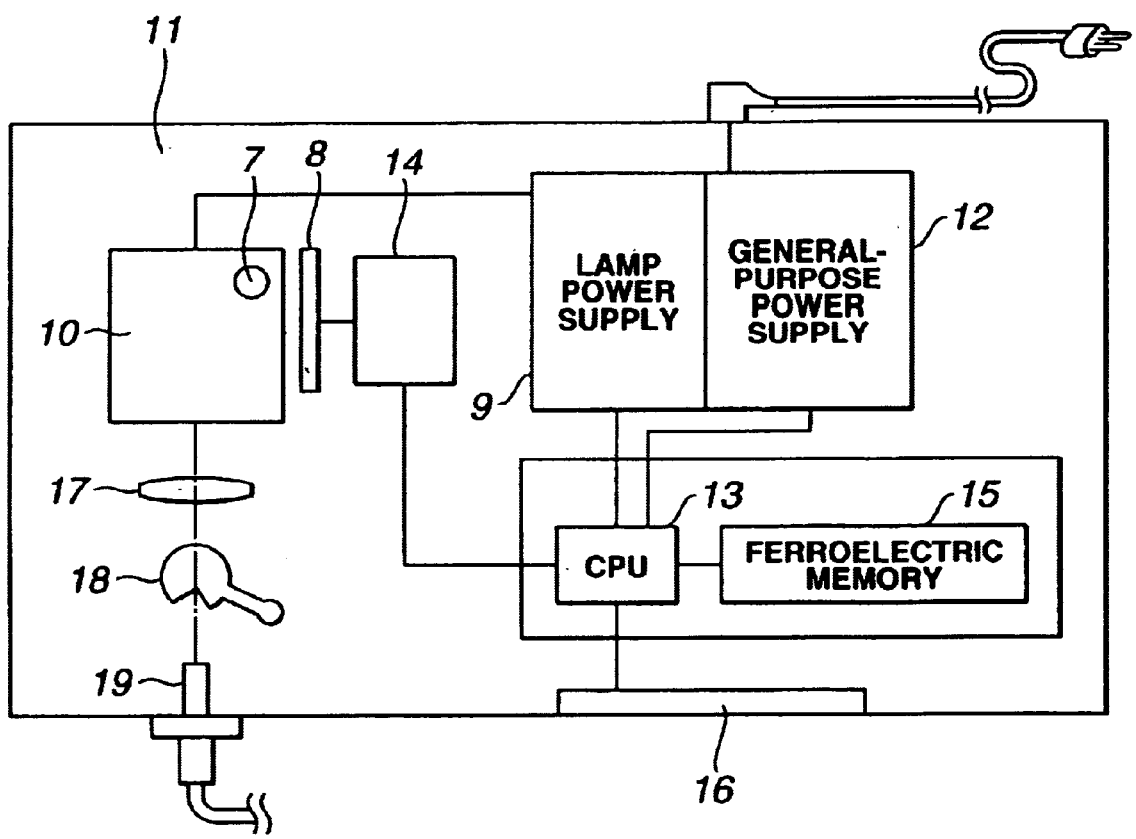
FIG. 2 is a block diagram illustrating the internal configuration of the light-source device.

FIG. 1 is a perspective view of a light-source device housing and a lamp unit illustrating a first embodiment of the present invention, and FIG. 2 is a block diagram illustrating the internal configuration of the light-source device.

In this regard, in the present embodiment, the present invention is applied to an endoscope light-source lamp.

As shown in FIG. 1, in an endoscope light-source device (hereinafter, referred to simply as a light-source device) of the first embodiment, an opening part 3 for installing the lamp unit (hereinafter, referred to simply as an opening part) is provided on one side of the device. The light-source device 1 has a lamp-unit container 2 connected to the opening part 3 in a device housing 11.

In the lamp-unit container 2, a lamp unit 10 can be installed in a removable manner. Also, in the lamp-unit container 2, a socket 6a to which a connector 6 of the lamp unit 10 is connected is disposed.

The lamp unit 10 has a lamp bracket 5 for holding a light-source lamp 4 and the connector 6 which connects the light-source lamp 4 to a lamp power-supply 9 (refer to FIG. 2).

In the present embodiment, the light-source device 1 is configured using an RFID (Radio Frequency IDentification)

system. In the RFID system, reading and rewriting of data is possible in a non-contact manner by communicating using radio waves or other electromagnetic waves.

The RFID system has a non-contact type data carrier which sends and receives radio-wave information in a non-contact manner. The non-contact type data carrier has a recording medium tag on which a predetermined pattern corresponding to the storage information is formed. The medium tag may be, for example, in the shape of a label, a cylinder, a card, a box, a coin, a stick, and so on.

In general, the non-contact type data carrier includes an antenna for sending and receiving radio waves, information communication means for receiving the radio wave information from outside by the antenna to get necessary power and information by, for example, electromagnetic induction and to oscillate the processing result, non-volatile information storage means for storing the radio wave information received by the information communication means and specific information in a readable manner, and control means for performing the processing for the exterior based on the information received by the communication means and the specific information stored in the information storage means.

In this regard, the information communication means can get necessary power and information by electromagnetic coupling, electrostatic coupling, a microwave technique, an optical technique, and so on, in addition to the electromagnetic induction method described above.

Thus, in the present embodiment, attention is given to the RFID system to be practically used for the light-source device.

This means that, in the present embodiment, the light-source device 1 has a structure in which a heat-resistant RFID tag 7 is fixed on the upper surface of the lamp bracket 5.

Figure 3:
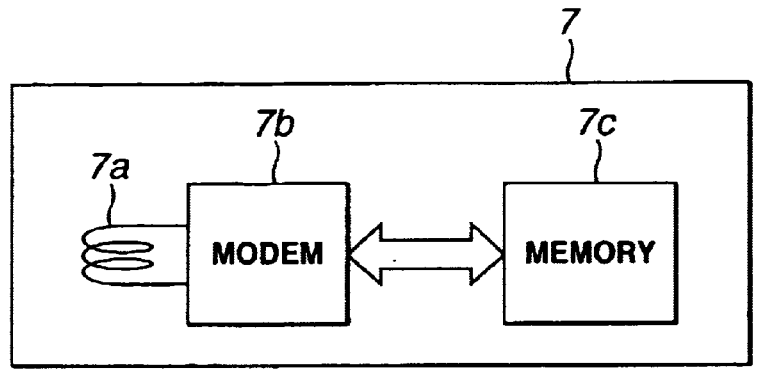
FIG. 3 is a schematic diagram of an RFID tag.

As shown in FIG. 3, the RFID tag 7 includes an antenna 7a for sending and receiving radio waves, a modulator-demodulator 7b for the radio waves sent and received by the antenna 7a, and a non-volatile memory unit (memory) 7c for reading and writing the modulated/demodulated information.

In the light-source device 1, as shown in FIG. 2, within the device housing 11, an antenna 8 for sending and receiving radio waves to the RFID tag 7, a controller 14 for driving and controlling the antenna 8, a CPU 13 for controlling the controller 14 and for measuring the operating time of the light-source lamp 4, thus functioning as a counter, a ferroelectric memory 15 which stores the information of the RFID tag 7 through the CPU 13 and is formed, for example, of on FRAM (Ferroelectric Random Access Memory), a lamp power supply 9 for supplying power to the light-source lamp 4 of the lamp unit 10, a general-purpose power supply 12, a condenser lens 17, a diaphragm 18, a light-guide connector 19, and so on are appropriately disposed.

Figure 4:
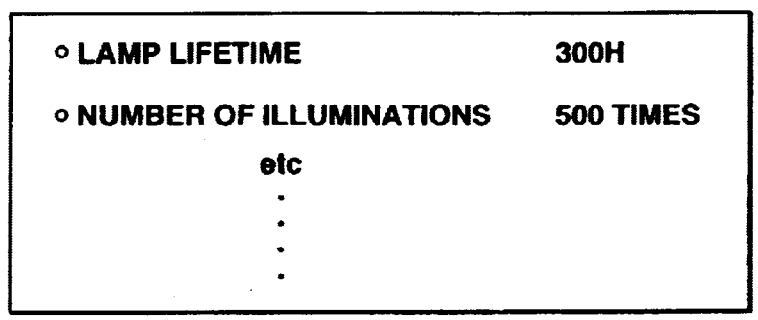
FIG. 4 illustrates information values displayed on the display part of a lifetime meter.

Also, the light-source device 1 is equipped with a display part 16 of a lifetime meter, which is formed by a liquid crystal panel, on the front panel of the device housing 11. As shown in FIG. 4, the display part 16 of the lifetime meter displays the lifetime of the lamp, the number of illuminations, and so on.

The lamp power-supply 9 supplies power to the light-source lamp 4 through the connector 6 in order for the light-source lamp 4 to emit light when the lamp unit 10 is installed.

The light emitted from the light-source lamp 4 is condensed by the condenser lens 17, and strikes the end face of the light-guide connector 19 through the diaphragm 18. The light-guide connector 19 is connected to a light-guide cap which is attached to the front face of the device housing 11. The light-guide connector 19 supplies the illuminating light of the light-source lamp 4 to a light-guide cable which is attached to the above-described light-guide cap. The light-guide cable transmits the illuminating light to a light guide of the endoscope, which is not shown in the figure. Then the endoscope irradiates the illuminating light transmitted by the light guide to an object in a cavity of a living body.

In this regard, the above-described general-purpose power supply 12 receives external electrical power and increases or decreases the voltage for transformation into the necessary power in order to supply power to the lamp power-supply 9, the CPU 13, and so on.

Next a description will be given of the operation of the light-source device 1 having such a configuration in accordance with the flowchart shown in FIG. 5.

The user installs the lamp unit 10 into the above-described lamp-unit container 2. In this way, the RFID tag 7 and the antenna 8 which reads and writes the information of the RFID tag 7 are placed close to each other within a distance which allows information to be sent and received.

For the RFID tag 7 and the antenna 8, an electromagnetic induction method is adopted. The electromagnetic induction method uses an electromagnetic wave in the long wave band, or the medium wave band having a frequency of 250 KHz or less, or within the 13.56 MHz band.

The RFID tag 7 and the antenna 8 use coils. It becomes possible for the RFID tag 7 and the antenna 8 to communicate each other by using the induction voltage derived from the induced magnetic flux of the two coils by electromagnetic induction.

Figure 5:
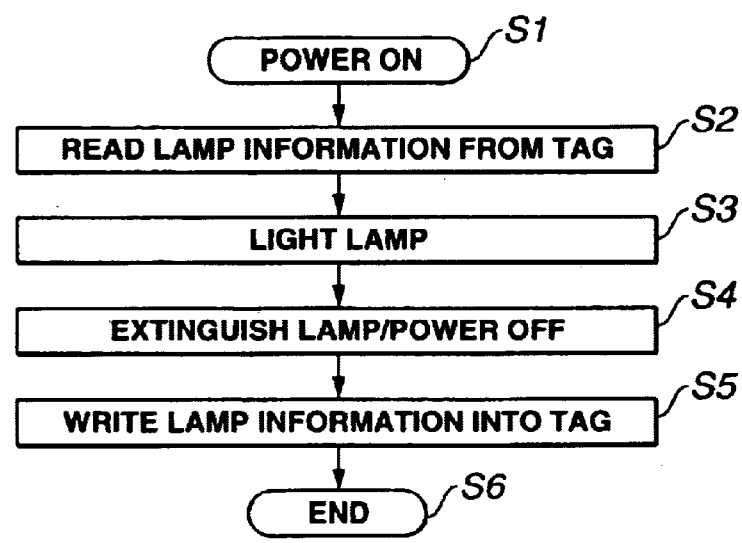
FIG. 5 is a flowchart illustrating the operation of the light-source device.

When the lamp unit 10 has been installed into the lamp-unit container 2, the user turns on the power (step S1), as shown by the flowchart in FIG. 5.

By doing this, using the antenna 8, the CPU 13 reads the total illumination time information up until the previous operation time, which is stored in the RFID tag 7, through the controller 14 to store the information in the ferroelectric memory 15 (step S2).

Thereafter the CPU 13 sends a signal for illuminating the light-source lamp 4 to the lamp power-supply 9 in order to illuminate the light-source lamp 4 (step S3).

The CPU 13 adds the current illumination time to the total illumination time which has been stored in the ferroelectric memory 15 to update the time. The illumination time is displayed on the display part 16 of the lifetime meter disposed on the front panel.

When the endoscope diagnosis and so on are complete, the power is turned off by the user in order to extinguish the lamp (step S4).

Immediately after this, the CPU 13 sends the latest total illumination time information to the RFID tag 7 through the antenna 8 to rewrite the information in the RFID tag 7 (step S5). Then the operation is complete (step S6).

In this regard, the power required immediately after turning off the power supply, is supplied using a capacitor such as a super-capacitor. Also, it is of course possible to use a special reader/writer to read and write data from and to the RFID tag 7.

Thus the light-source device 1 of the present embodiment has a configuration in which the readable/writable non-contact type RFID tag 7 is disposed on the light-source lamp 4, and an antenna 8 for accessing the RFID tag 7, a controller 14 for driving the antenna 8, and a CPU 13 for controlling the controller 14 are disposed in the housing of the device.

Consequently, the light-source device 1 of the present embodiment can write the number of illuminations of the light-source lamp 4, the illumination time, and so on from the CPU 13 to the above-described RFID tag 7 through the controller 14 and the antenna 8.

Additionally, the light-source device 1 of the present embodiment can read the RFID tag 7, in which data is written, by the antenna 8 and the controller 14, perform data processing in the CPU 13, and display the result on the lifetime meter disposed on the front panel.

Accordingly, the light-source device 1 of the present embodiment can read and display the information of the light-source lamp 4 correctly even if various kinds of lamp units 10 are installed. Thus, the light-source device 1 of the present embodiment enables users, service personnel, and so on to know the correct time for replacing the light-source lamp.

(Second Embodiment)

Figures 6, 7:
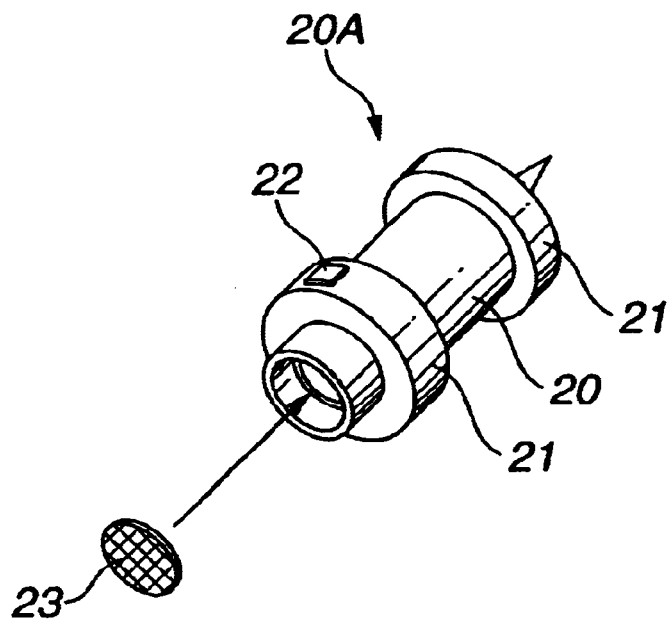
FIG. 6 is a perspective view of a lamp unit having a xenon lamp to be used for the light-source device according to a second embodiment of the present invention.
FIG. 7 is a table illustrating an example of the standard values at delivery time of the xenon lamp.
Figure 8:
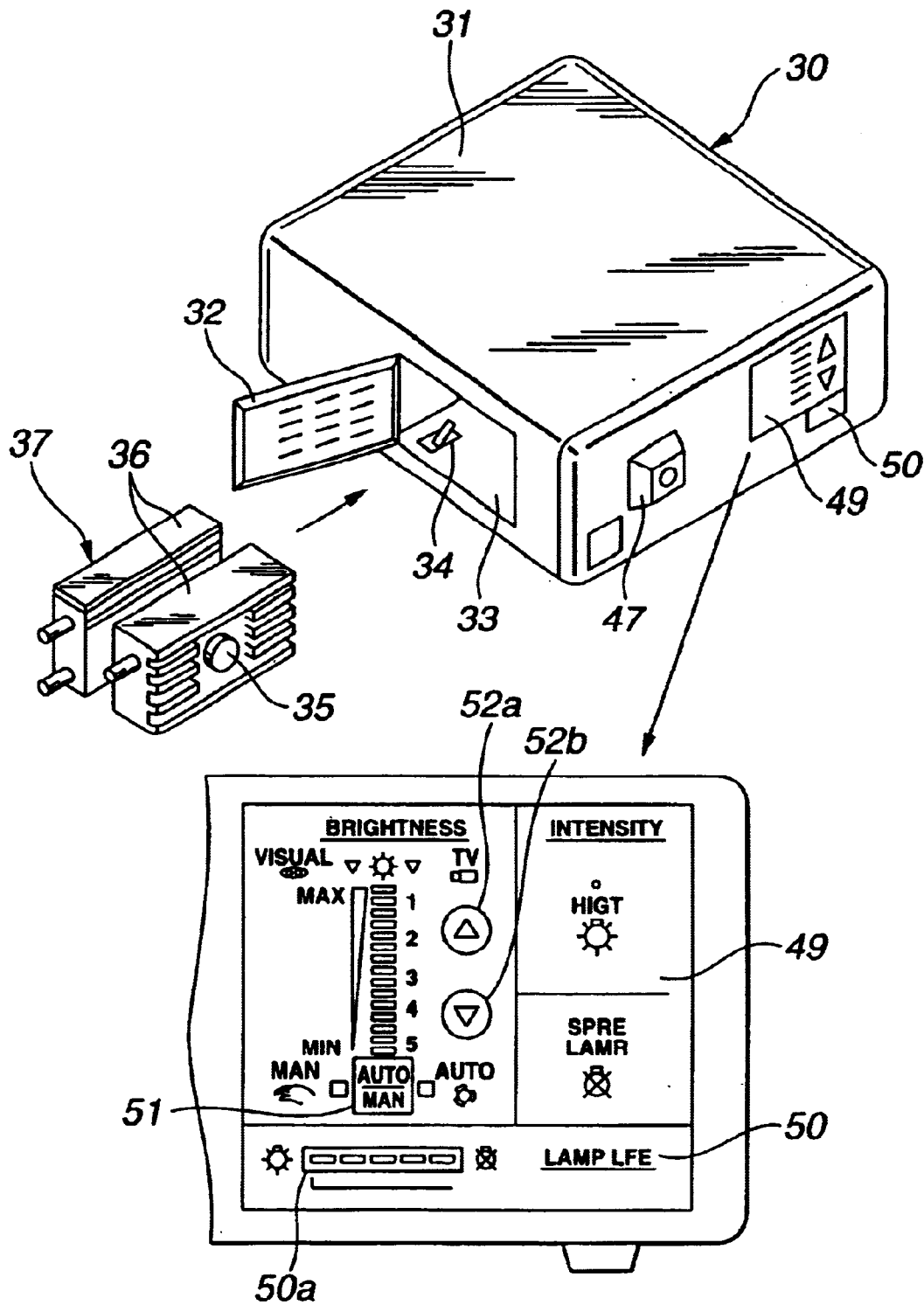
FIG. 8 is a perspective view and a partly enlarged view illustrating an endoscope light-source device having a conventional lifetime meter.
Figure 9:
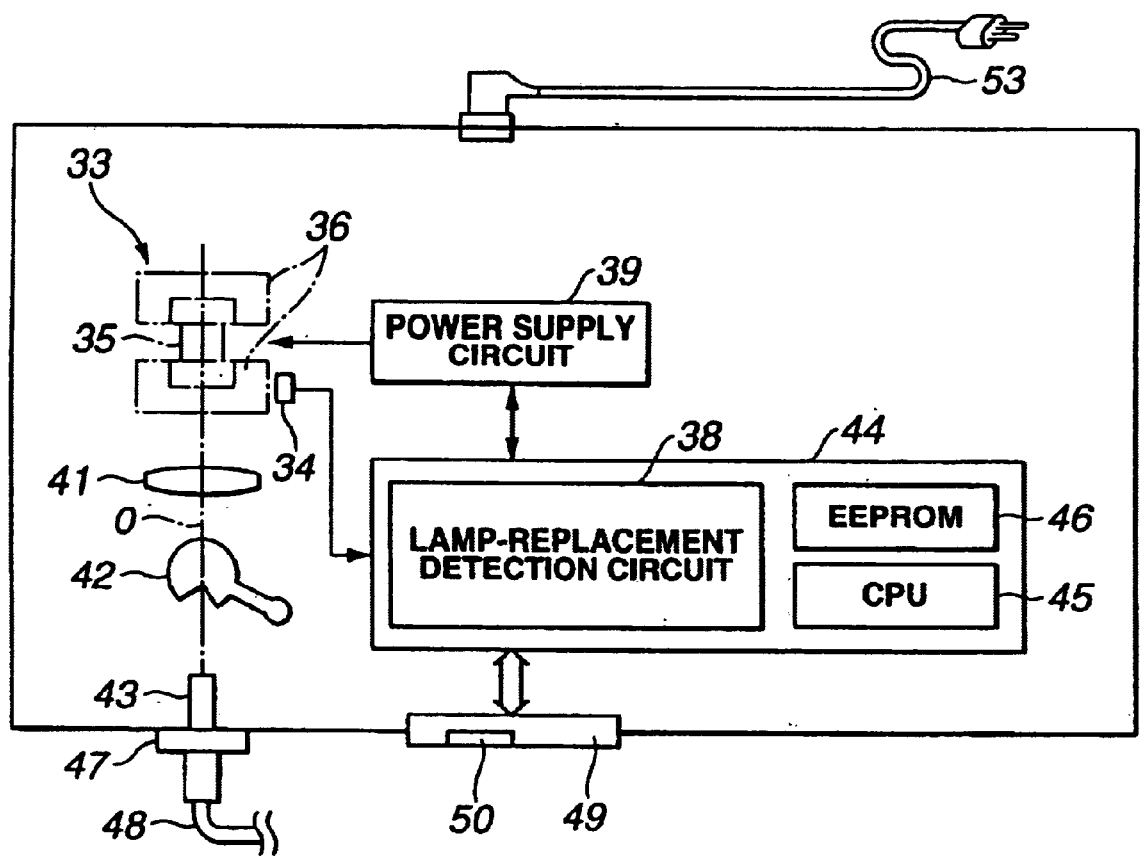
FIG. 9 is a block diagram illustrating the configuration of the endoscope light-source device shown in FIG. 8.

FIG. 6 is a perspective view of a lamp unit having a xenon lamp to be used for the light-source device according to a second embodiment of the present invention, and FIG. 7 is a table illustrating an example of standard values at delivery-time of the xenon lamp shown in FIG. 6.

In the second embodiment, an RFID tag is disposed on the lamp unit.

The light-source device of the second embodiment has a configuration including a lamp unit 20A which uses a bombshell-shaped xenon lamp (hereinafter simply referred to as a xenon lamp) 20 as shown in FIG. 6. The lamp unit 20A is equipped with heat sinks 21 at both the anode side and the cathode side in order to cool the xenon lamp 20.

Here, the conventional xenon lamp has standard values which have been determined at delivery time. In order to keep the amount of light emitted from the lamp corresponding to each of the standard values constant, the conventional xenon lamp is equipped with several kinds of filters selected at the time of delivery to a customer. Consequently, for conventional xenon light-sources, the inspection of the brightness of every lamp is performed in order to attach the brightness data to every lamp.

Accordingly, in the conventional xenon lamp, if the xenon lamp is too bright, a special dimmer filter is incorporated for delivery in order to prevent burning of the light guide. Thus, in the case of the conventional xenon lamp, the delivery procedure is laborious and there is the possibility that the brightness varies a lot at the user's site.

In the second embodiment, the lamp unit 20A is equipped with the RFID tag 22 on one heat sink 21.

Also, in the lamp unit 20A, each of the standard values at delivery time is registered in the RFID tag 22 as information in advance. The registration is performed at delivery time by writing the information into the RFID tag 22 using a reader/writer having an antenna, which is not shown in the figure.

The standard values at delivery time which are written into the RFID tag 22 are represented by predetermined numeric values, as shown in FIG. 7. The current values within the specific range considered to be most suitable accompany these values.

In the light-source device of the second embodiment, having such a configuration, the information registered in the RFID tag 22 is read, for example, by the antenna 8 in the device housing under the control of the CPU 13 shown in FIG. 2 in the first embodiment.

Then, in the light-source device, the CPU 13 sets the lamp current value which is most suitable for the standard value at delivery time. The CPU 13 sends the signal of the lamp current value which has been set to the lamp power-supply 9. By doing this, the lamp power-supply 9 supplies the current value that is most suitable for the standard value at delivery time information to the xenon lamp 20.

Accordingly, the light-source device of the second embodiment can emit the optimum amount of light without providing the xenon lamp 20 with the dimmer filter 23. Accordingly, the light-source device of the second embodiment can eliminate the conventional problem, thereby making it possible to easily obtain the optimum brightness.

In the present invention, it is obvious that various different embodiments can be made based on the present invention without departing from the spirit and the scope of the invention. The present invention will not be limited by the specific embodiments except as restricted by the appended claims.

What is claimed is:

1. A light-source device comprising:
   a lamp unit having a light-source lamp;
   a container part for removably containing the lamp unit;
   a counter for measuring illumination time information of the light-source lamp when the lamp unit is installed in the container part;
   a first antenna for sending the illumination time information measured by the counter to the lamp unit;
   a second antenna, which is provided in the lamp unit, for receiving the illumination time information which is sent from the first antenna; and
   a rewritable memory, which is provided in the lamp unit, for storing the illumination time information received by the second antenna.

2. The light-source device according to claim 1, further comprising:
   a controller for demodulating illumination time information received by the first antenna to output the information to the counter and for modulating illumination time information measured by the counter to output the information to the first antenna; and
   a modulator-demodulator circuit, which is provided in the lamp unit, for reading and modulating illumination time information stored in the memory to output the information to the second antenna and for demodulating illumination time information to write the information into the memory.

3. The light-source device according to claim 2,
   wherein the modulator-demodulator circuit, the second antenna, and the memory are provided in a tag.

4. The light-source device according to claim 2,
   wherein the counter controls the controller to read total illumination time information up until the previous illumination, which is stored in the memory, from the first antenna when the lamp unit is installed in the container part.

5. The light-source device according to claim 3,
   wherein the tag is a non-contact type tag.

6. The light-source device according to claim 4, further comprising a ferroelectric memory for storing the total illumination time information up until the previous illumination, which has been read,
   wherein the counter adds illumination time measured for the present illumination to the total illumination time up until the previous illumination, which has been stored in the ferroelectric memory.

7. The light-source device according to claim 4,
   wherein the counter displays the total illumination time information up until the previous illumination, which has been read.

8. The light-source device according to claim 4,
wherein the counter adds the illumination time measured for the present illumination to the total illumination time up until the previous illumination immediately after a power supply is turned off.

9. The light-source device according to claim 5,
wherein the non-contact type tag is an RFID (Radio Frequency Identification) tag.

10. The light-source device according to claim 6,
wherein the counter displays the illumination time information to which the illumination time measured for the present illumination has been added.

11. The light-source device according to claim 6,
wherein the illumination time information includes at least one of the total illumination time up until the previous illumination of the light-source lamp, the total number of illuminations, the brightness, standard values, and identification information.

12. The light-source device according to claim 6,
wherein the counter varies the electrical power output to the light-source lamp based on the brightness or standard values of the light-source lamp.

13. The light-source device according to claim 6,
wherein the counter varies the electrical power output to the light-source lamp based on identification information of the light-source lamp.

14. A light-source device comprising:

a lamp unit having a light-source lamp;

a device housing having a container part for removably containing the lamp unit;

a counter, which is provided in the device housing, for measuring illumination time information of the light-source lamp;

a first antenna, which is provided in the device housing, for sending the illumination time information measured by the counter to the lamp unit;

a controller, which is provided in the device housing, for demodulating the illumination time information received by the first antenna to output the information to the counter and for modulating illumination time information measured by the counter to output the information to the first antenna;

a second antenna, which is provided in the lamp unit, for receiving the illumination time information which is sent from the first antenna;

a rewritable memory, which is provided in the lamp unit, for storing the illumination time information received by the second antenna; and a modulator-demodulator circuit, which is provided in the lamp unit, for reading and modulating illumination time information stored in the memory to output the information to the second antenna and for demodulating illumination time information received by the second antenna to write the information into the memory.

15. The light-source device according to claim 14,
wherein the modulator-demodulator circuit, the second antenna, and the memory are provided in a tag.

16. The light-source device according to claim 14,
wherein the counter controls the controller to read the total illumination time information up until the previous illumination, which is stored in the memory, from the first antenna when the lamp unit is installed in the container part.

17. A light-source device comprising:

a lamp unit having a light-source lamp;

a device housing having a container part for removably containing the lamp unit;

a rewritable memory for storing illumination time information of the light-source lamp;

wireless reading means for reading the illumination time information from the memory;

a counter for measuring illumination time of the light-source lamp and adding the measured illumination time to a total illumination time information which has been read by the reading means; and wireless writing means for writing the total illumination time information to which the illumination time has been added by the counter into the memory.

18. The light-source device according to claim 17,
wherein the illumination time information includes at least one of the total illumination time up until the previous illumination of the light-source lamp, the total number of illuminations of the light-source lamp, a brightness of the light-source lamp, standard values of the light-source lamp, and identification information of the light-source lamp.

19. The light-source device according to claim 18,
wherein the counter varies the electrical power output to the light-source lamp based on at least one of the brightness and standard values of the light-source lamp.

20. The light-source device according to claim 18,
wherein the counter varies the electrical power output to the light-source lamp based on identification information of the light-source lamp.

* * * * *